United States Patent
Salomonson et al.

(10) Patent No.: US 6,238,601 B1
(45) Date of Patent: May 29, 2001

(54) METHOD FOR MAKING CERAMIC ARTIFICIAL DENTAL BRIDGES

(75) Inventors: Jonas Salomonson, Huddinge; Agneta Odén, Stocksund, both of (SE)

(73) Assignee: Sandvik AB, Sandviken (SE)

( * ) Notice: Subject to any disclaimer, the term of this patent is extended or adjusted under 35 U.S.C. 154(b) by 0 days.

(21) Appl. No.: 09/486,609

(22) PCT Filed: Sep. 11, 1998

(86) PCT No.: PCT/SE98/01620

§ 371 Date: May 18, 2000

§ 102(e) Date: May 18, 2000

(87) PCT Pub. No.: WO99/13795

PCT Pub. Date: Mar. 25, 1999

(30) Foreign Application Priority Data

Sep. 12, 1997 (SE) .................................................. 9703311

(51) Int. Cl.$^7$ ...................................................... A61C 13/00
(52) U.S. Cl. ........................ 264/16; 156/182; 156/283; 156/325; 264/18
(58) Field of Search .................. 264/16, 18; 156/182, 156/283, 325; 433/191, 171

(56) References Cited

U.S. PATENT DOCUMENTS

| | | | | |
|---|---|---|---|---|
| 4,265,669 | * | 5/1981 | Starling et al. | 106/73.4 |
| 4,634,561 | * | 1/1987 | Deluca | 264/17 |
| 4,744,757 | * | 5/1988 | Adair et al. | 433/180 |
| 5,080,589 | | 1/1992 | Odén et al. | 433/202.1 |
| 5,342,201 | | 8/1994 | Odén | 433/223 |
| 5,447,967 | * | 9/1995 | Tyszblat | 523/116 |

* cited by examiner

Primary Examiner—Christopher A. Fiorilla
(74) Attorney, Agent, or Firm—Burns, Doane, Swecker & Mathis, L.L.P.

(57) ABSTRACT

A method for making artificial tooth bridges having a ceramic densely sintered high strength individual core veneered with porcelain using powder metallurgical methods, wherein the individual bridge parts are joined together as a bridge core with glass, which in molten condition wets the ceramic core material. The glass therefore finds its way into the gap between the bridge parts and reacts with the ceramics so that during cooling it forms a strong joint between the individual densely sintered ceramic bridge parts.

8 Claims, 1 Drawing Sheet

METHOD FOR MAKING CERAMIC ARTIFICIAL DENTAL BRIDGES

This Application is a 371 of PCT/SE98/01620 filed Sep. 11, 1998.

FIELD OF THE INVENTION

The present invention relates to a method for making artificial dental bridges accurate to shape in high strength ceramic material with powder metallurgical methods as well as by joining of two or more ceramic parts to each other.

BACKGROUND OF THE INVENTION

U.S. Pat. No. 5,342,201 discloses a method of manufacturing artificial tooth restorations to natural teeth or implants consisting of a ceramic densely sintered high strength core veneered with dental porcelain by powder metallurgical methods.

OBJECT AND SUMMARY OF THE INVENTION

The object of the present invention is to achieve a rational manufacturing technique for dental bridges in densely sintered high strength ceramic material using modern powder metallurgical technique, registering technique and joining technique. Dental bridges in e.g. densely sintered high strength alumina offer a combination of mechanical strength, biocompatibility and esthetics which is generally not possible with established dental materials and methods intended for dental bridges.

The present invention relates to a method of manufacturing artificial dental bridges in densely sintered ceramic material by joining two or more densely sintered ceramic parts with the aid of glass or sintering technique. The individual parts, whose inner surface which should fit against one or more prepared tooth surfaces or artificial abutments, are made by forming a ceramic powder mixture against a surface of a body whereby said surface is made using a three-dimensional optical or mechanical reading method in which the surfaces of the prepared teeth or artificial abutments and their mutual relationship are registered, either directly in the mouth or on a model in e.g. plaster whereafter the registered surfaces are reproduced in an enlarged format e.g. with the aid of a computer controlled milling machine whereby the magnification is calculated considering the shrinkage of the ceramic material during sintering to full density with addition of desired gap required for cement according to U.S. Pat. No. 5,342,201 and U.S. Pat. No. 5,080,589.

DETAILED DESCRIPTION OF THE PREFERRED EMBODIMENTS

Figure 1:
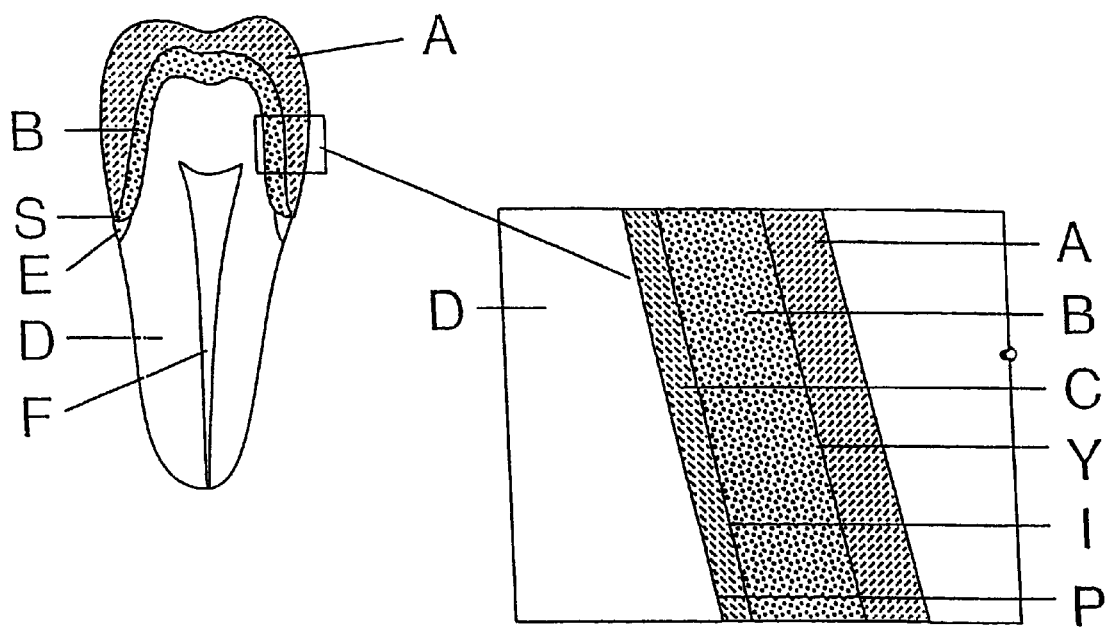
FIG. 1 is a cross-sectional view of a natural tooth with an artificial tooth crown.

FIG. 1 shows a cross section of a natural tooth with an artificial tooth crown. In this figure, A=dental porcelain, B=core, Y=outer surface of the core, I=inner surface of the core, C=cement, P=prepared surface of the tooth, S=preparation border, E=enamel, D=dentin and F=pulp.

Figure 2:
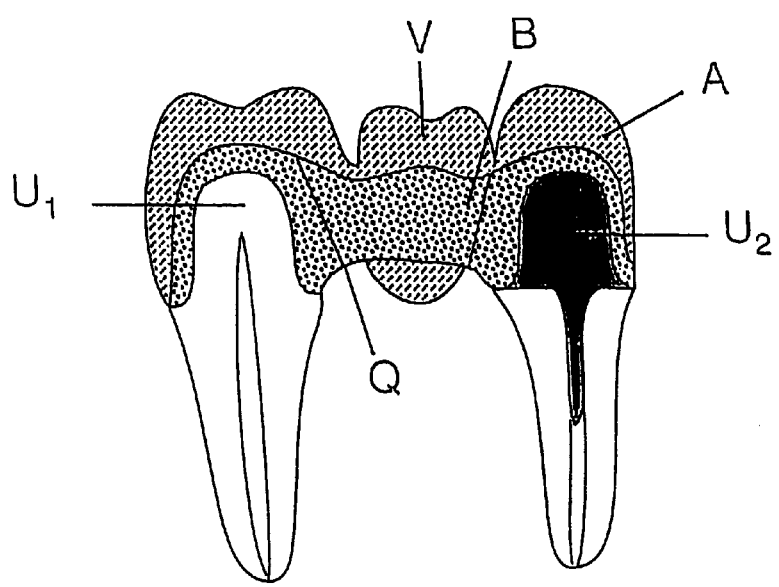
FIG. 2 is a cross-sectional view of two teeth and a bridge.

FIG. 2 shows a cross-section of a bridge containing three joined parts. The bridge is cemented on two supporting teeth. These supporting teeth may have a vital abutment (U1) or an artificial abutment (U2) manufactured in some dental alloy, ceramic material or some reinforced polymer. The bridge contains two artificial tooth crowns according to FIG. 1 and with a central pontic (V), as a substitute for a lost tooth. These units are joined at high temperature through addition of a glass, which in melted condition wets the core material and spreads into the gap between the individual bridge parts. During cooling the glass will solidify and a high strength joint (Q) joining the bridge units is obtained. The bridge consists of a core (B) with veneered dental porcelain (A). A bridge can be cemented on more than two supporting prepared teeth and thus contain more than one pontic. The supporting teeth can also be prepared for inlays or veneers. Veneers can be made for both buccal and lingual surfaces. The supporting teeth can even be implants or artificial abutments.

As shown in FIG. 2, the individual ceramic bridge parts have compatible joining portions shaped to obtain a mechanical locking with each other. This mechanical locking provides optimal strength under pressure when the parts are joined.

As is shown in FIG. 2 artificial dental bridges are made as a core in densely sintered ceramic (B) with veneered dental porcelain (A). The core consists of two or more parts joined together with glass which is heat-treated and joins by melting/solidification. The bridge is fixed against the abutments (U1) and (U2) by e.g. cementing.

The ceramic powder can be made of several methods well known to the skilled artisan. Traditional powder metallurgical technique can be used, where the different components are mixed and milled in dry or wet condition with water or a solvent e.g. alcohol, as a milling liquid. To the ceramic slurry, lubricants or other organic binders, are added when needed at a suitable time in the process.

The ceramic base material of the core comprises preferably one or more biocompatible oxides (including phosphates, silicates and sulphates), with additives of carbides, silicides, nitrides or borides with or without binder metal in addition to conventional sintering aids. The base material can also comprise other high performance ceramics which are biocompatible such as nitrides, oxynitrides, sulphides, oxysulphides or similar phases as well as of ceramic materials containing halogens. Examples of biocompatible oxides, which can form base matrix for the ceramic body, are oxides such as $Al_2O_3$, $TiO_2$, $MgO$, $ZrO_2$ and $ZrO_2$ with additives of smaller amounts of up to 10 mol % $Y_2O_3$ or $MgO$ (partly or completely stabilized $ZrO_2$). In a preferred embodiment the ceramic material comprises >50%, preferably >85%, $Al_2O_3$ with additives of conventional sintering aids. It is important that the ceramic material is sintered to closed porosity, which for an oxide material means at least 98% of theoretical density, but in order to ensure good mechanical strength, the material should preferably have a density over 99% with densities over 99.5% giving the best strength.

According to the present invention the bridge units such as tooth copings and one or more pontics as substitute for lost teeth are made with the technique according to U.S. Pat. No. 5,342,201 and U.S. Pat. No. 5,080,589. As an alternative to the conventional technique with pressing and sintering the body can be produced by EPD (Electrophoretic Deposition) in order to subsequently be sintered in a conventional manner. The bridge units should subsequently be joined with a high demand on strength and fit on the joined bridge. In order to obtained an acceptable fit the bridge units should remain in their mutual positions during the whole joining process. By performing the joining process with the bridge units placed on a refractory die e.g. a refractory replica of the base model of the situation in the mouth, the position of the bridge units can be locked during the joining process and it is possible to obtain optimal fit. A glass can be used as joining material which has to have the characteristic properties of wetting the densely sintered ceramic material i.e. the glass should have a lower surface energy at the temperature used during the joining process than the ceramic material in the bridge units. This melted glass will easily spread out over the surfaces of the bridge units in order to lower their surface energy. The melted glass must have a low viscosity in order to be able to spread into in the gap between the bridge units. Furthermore, the glass should have the characteristic property that it reacts, not too little and not too much, with the ceramic material in the bridge units in order to get an optimal bond between glass and ceramic material in the joint. In order to obtain this the glass should contain the same metal oxides as the material in the bridge units. This amount should be less than saturation level of the mentioned metal oxides in the glass at the joining temperature. The thermal expansion coefficient must be lower than or equal to the ceramic material in the bridge units in order to avoid development of fractures during cooling. The melting temperature of the glass must be higher than the melting temperature of the veneering porcelain in order to avoid distortion of the bridge during the subsequent firing of porcelain. The joint should be designed so that a certain mechanical locking is obtained in the direction of the main force in order to obtain an optimal strength. If the joining process of the bridge units is made with a correct refractory replica of the base model, a correctly shaped joint and with a glass with properties according to above the joined bridge becomes very strong in compression at the same time as the fit can be optimal. An example of important main constituents in a glass composition that works well when joining highly pure alumina is: $SiO_2$ 32 mol %, $B_2O_3$ 24 mol %, $Al_2O_3$ 18 mol % as well as $La_2O_3$ 12 mol %. A bridge joined with glass, can subsequently be veneered with one or more layers of dental porcelain in order to obtain a good esthetics. The advantage with manufacturing bridges with the technique according to the present invention is that e.g. densely sintered high strength alumina can be joined together which results in a dental bridge with high strength, optimal fit and an esthetics which can not be obtained with conventional dental bridges of e.g. metal ceramics.

What is claimed is:

1. A method of making artificial dental bridges comprising the steps of:

providing individual ceramic bridge parts having compatible joining portions shaped to obtain a mechanical locking with each other; and sealing the individual ceramic bridge parts in their mechanical locking positions with glass placed along their joining portions to form a bridge core, wherein the glass in melted condition wets the ceramic core material and therefore spreads into a gap between the bridge parts and reacts with the ceramic such that the glass during cooling forms a strong joint between the individual ceramic bridge parts thereby reinforcing the mechanical locking of the individual ceramic bridge parts.

2. A method of making artificial dental bridges having a ceramic densely sintered high strength individual core veneered with porcelain by powder metallurgical methods comprising the steps of:

providing individual densely sintered ceramic bridge parts having compatible joining portions shaped to obtain a mechanical locking with each other; and sealing the individual densely sintered ceramic bridge parts in their mechanical locking positions with glass placed along their joining portions to form a bridge core, wherein the glass in melted condition wets the ceramic core material and therefore spreads into a gap between the bridge parts and reacts with the ceramic such that the glass during cooling forms a strong joint between the individual densely sintered ceramic bridge parts thereby reinforcing the mechanical locking of the individual densely sintered ceramic bridge parts.

3. A method according to claim 2 wherein the ceramic core material comprises a high strength ceramic material with a relative density >98%.

4. A method according to claim 2 wherein the ceramic core material comprises one or more of the oxides $Al_2O_3$, $TiO_2$, MgO, $ZrO_2$ or $ZrO_2$ with up to 10 mol % $Y_2O_3$, MgO or CaO.

5. A method according to claim 2 wherein the glass being used for joining has a surface energy at a joining temperature lower than the surface energy for the ceramic core material.

6. A method according to claim 2 wherein the glass comprises the same metal oxides as the ceramic core material in an amount that falls below the degree of saturation of the mentioned metal oxides in the glass at a joining temperature.

7. A method according to claim 2 wherein the glass has a coefficient of thermal expansion which is lower than or the same as the coefficient of thermal expansion of the ceramic core material.

8. A method according to claim 2 wherein the glass comprises the following main constituents: $SiO_2$ 32 mol %, $B_2O_3$ 24 mol %, $Al_2O_3$ 18 mol % as well as $La_2O_3$ 12 mol %.

* * * * *